(12) United States Patent
Vats et al.

(10) Patent No.: US 9,504,655 B2
(45) Date of Patent: Nov. 29, 2016

(54) CAPSULE DOSAGE FORM OF METOPROLOL SUCCINATE

(71) Applicant: SUN PHARMACEUTICAL INDUSTRIES LIMITED, Mumbai, Maharashtra (IN)

(72) Inventors: Sandeep Kumar Vats, Sonipat (IN); Balaram Mondal, East Midnapore (IN); Kalaiselvan Ramaraju, Tiruchirappalli (IN); Romi Barat Singh, Varanasi (IN)

(73) Assignee: SUN PHARMACEUTICAL INDUSTRIES LIMITED, Mumbai (IN)

( * ) Notice: Subject to any disclaimer, the term of this patent is extended or adjusted under 35 U.S.C. 154(b) by 0 days.

(21) Appl. No.: 15/012,775

(22) Filed: Feb. 1, 2016

(65) Prior Publication Data
US 2016/0143856 A1 May 26, 2016

Related U.S. Application Data

(63) Continuation of application No. PCT/IB2015/055195, filed on Jul. 9, 2015.

(60) Provisional application No. 62/022,316, filed on Jul. 7, 2014.

(51) Int. Cl.
*A61K 9/48* (2006.01)
*A61K 9/50* (2006.01)
*A61J 3/07* (2006.01)
*A61K 31/138* (2006.01)

(52) U.S. Cl.
CPC .............. *A61K 9/4808* (2013.01); *A61J 3/071* (2013.01); *A61K 9/485* (2013.01); *A61K 9/4858* (2013.01); *A61K 9/4866* (2013.01); *A61K 9/5078* (2013.01); *A61K 31/138* (2013.01)

(58) Field of Classification Search
None
See application file for complete search history.

(56) References Cited

U.S. PATENT DOCUMENTS

| | | | |
|---|---|---|---|
| 5,246,714 A | 9/1993 | Dahlinder et al. | 424/497 |
| 6,156,342 A * | 12/2000 | Sriwongjanya | A61K 31/135 424/464 |
| 2008/0113031 A1* | 5/2008 | Moodley | A61K 9/5073 424/490 |

FOREIGN PATENT DOCUMENTS

| | | | | |
|---|---|---|---|---|
| IN | WO 2009087663 A2 * | 7/2009 | | A61K 9/2866 |
| WO | WO 2009/087663 | 7/2009 | | |

* cited by examiner

*Primary Examiner* — Robert A Wax
*Assistant Examiner* — Quanglong Truong

(57) ABSTRACT

The present invention provides an extended-release capsule dosage form of metoprolol succinate in the form of coated discrete units and processes for their preparation.

19 Claims, No Drawings

CAPSULE DOSAGE FORM OF METOPROLOL SUCCINATE

FIELD OF THE INVENTION

The present invention provides an extended-release capsule dosage form of metoprolol succinate in the form of coated discrete units and processes for their preparation.

BACKGROUND OF THE INVENTION

Metoprolol is a beta-blocker that is prescribed for the treatment of hypertension, angina pectoris, and stable, symptomatic heart failure. Currently, the marketed extended-release dosage form of metoprolol succinate is a multiparticulate tablet dosage form comprising silicon dioxide beads as an inert core (Toprol-XL® tablet).

U.S. Pat. No. 5,246,714 discloses a controlled-release preparation containing a number of insoluble beads coated with one or more pharmaceutically active compounds. It further discloses examples of insoluble materials such as silicon dioxide, glass, or plastic resin particles.

Compression of multiparticulates into a tablet dosage form is a challenging task. An additional 30% to 60% of tableting excipients are necessary to avoid any damage to the polymer coat and to retain the functional properties of the coat during compression. However, even after the process and excipient optimizations, cracks in the extended-release polymer coat are observed at the commercial scale. These cracks in the extended-release polymer coat impact the dissolution profile of the dosage form.

A capsule dosage form of coated multiparticulates offers an advantage over the tablet dosage form, as it avoids the compression step. Further, this dosage form is easier to swallow and requires the addition of fewer excipients than the tablet dosage form.

Therefore, there is a need in the art to prepare an alternate extended-release dosage form of metoprolol succinate which is bioequivalent to the marketed Toprol-XL® tablet.

SUMMARY OF THE INVENTION

The present invention provides an extended-release capsule dosage form of metoprolol succinate in the form of coated discrete units, wherein said capsule dosage form is bioequivalent to the marketed Toprol-XL® tablet. Moreover, the extended-release capsule dosage form comprising coated discrete units can be sprinkled onto food to ease administration for patients who have difficulty swallowing tablets or capsules, e.g., pediatric patients and geriatrics.

DETAILED DESCRIPTION OF THE INVENTION

A first aspect of the present invention provides an extended-release capsule dosage form of metoprolol succinate in the form of coated discrete units, wherein the capsule dosage form comprises metoprolol succinate in an amount of about 30% to about 70% by total weight of the dosage form and is bioequivalent to the marketed Toprol-XL® tablet.

According to one embodiment of this aspect, the extended-release capsule dosage form is in the form of a sprinkle capsule.

According to another embodiment of this aspect, the sprinkle capsule dosage form may be sprinkled onto soft food, e.g., applesauce, yogurt, or pudding, at the time of administration.

According to another embodiment of this aspect, the extended-release capsule dosage form comprises coated discrete units having a particle size from about 0.2 mm to 2.5 mm.

According to another embodiment of this aspect, the extended-release capsule dosage form in the form of coated discrete units comprising:
a) inert cores;
b) a drug layer over the inert cores comprising metoprolol succinate; and
c) an extended-release layer over the drug layer.

The term "extended-release" includes controlled-release, modified-release, and sustained-release. The capsule dosage form is stable and has a similar release profile as compared to the Toprol-XL® tablet throughout the shelf life of the product. Metoprolol succinate may be present in an amount of about 30% to about 70% by total weight of the dosage form. In particular, about 40% to about 60% by total weight of the dosage form, wherein the capsule shell weight is not included in the total weight of the dosage form.

Metoprolol succinate of the present invention may be in racemic form or as a pure enantiomer. Further, metoprolol succinate may be present in the capsule dosage form in a strength of about 25 mg to about 200 mg. Coated discrete unit comprising metoprolol in a strength of 25 mg/50 mg, 100 mg, and 200 mg may be filled in size 4, size 2, and size 0 hard gelatin capsules, respectively.

The term "discrete units," as used herein, refers to coated inert cores in the form of plurality of pellets, granules, minitablets, or beads.

Bioequivalence is established by comparing pharmacokinetic parameters, for example AUC and $C_{max}$, of the present invention with Toprol-XL® tablets in healthy human subjects.

The term "AUC" refers to the area under the time/plasma concentration curve after the administration of the metoprolol succinate extended-release dosage form to healthy human subjects.

The term "$C_{max}$" refers to the maximum concentration of metoprolol in the blood following the administration of the metoprolol succinate extended-release dosage form to healthy human subjects.

The extended-release capsule dosage forms of metoprolol succinate are stable when subjected to the stability conditions of 40° C. and 75% RH for 6 months. Further, the coated discrete units would be stable when sprinkled on to the soft food for at least 10 minutes.

Inert cores may be selected from the group comprising of water-soluble or water-swellable cores.

According to another embodiment of this aspect, water-soluble or water-swellable inert cores are made up of sugar, microcrystalline cellulose, cellulose, starch, modified starch, or mixtures thereof.

According to another embodiment of this aspect, the inert core is a sugar core wherein said sugar is selected from the group consisting of glucose, mannitol, lactose, xylitol, dextrose, and sucrose.

Coated discrete units may be prepared by coating a drug layer comprising metoprolol succinate, optionally along with other pharmaceutically acceptable excipients, onto an inert core. Optionally, a seal coat layer may be present between the inert core and the drug layer. The seal coat may further comprise film-forming polymers. Further, the drug layer coated cores are coated with an extended-release layer.

According to one embodiment of this aspect, the extended-release layer comprises water-soluble/swellable polymers, water-insoluble polymers, or mixtures thereof.

The extended-release layer is present in an amount of 5% to 30% based on the weight of the drug layer coated cores.

Water-soluble/swellable polymers include hydroxypropyl methylcellulose having an apparent viscosity ranging from 100 cP to 150,000 cP (2% in water at 20° C.), e.g., K100, K4M, K15M, K100M, E4M, and E10M; hydroxypropyl cellulose, e.g., HPC-H, HPC-M, HPC-HF, and HPC-HXF; polyethylene glycol (molecular weight of about 3000 or above); poly(ethylene oxide), e.g., PEO-27, PEO-18, PEO-15, PEO-8, PEO-4, Polyox®WSR-1105, and Polyox® WSR-303; hydroxyethyl cellulose; carboxymethyl cellulose; xanthan gum; polyvinyl pyrrolidone; starch; and mixtures thereof.

Water-insoluble polymers include cellulose ethers, e.g., ethyl cellulose; cellulose esters, e.g., cellulose acetate; polymethacrylic acid esters copolymers, e.g., Eudragit® NE 30 D and Eudragit® NE 40 D; aminoalkyl methacrylate copolymers, e.g., Eudragit® RL 100, Eudragit® RL PO, Eudragit® RS PO, and Eudragit® RS 100; copolymers of polyvinyl acetate and polyvinyl pyrrolidone, e.g., Kollidon® SR; and mixtures thereof. In particular, the extended-release polymer is a water-insoluble polymer. More particularly, the water-insoluble polymer is ethyl cellulose.

The extended-release polymer may be present in an amount of 50% to 99% based on the weight of the extended-release layer.

According to another embodiment of this aspect, the extended-release layer comprises a water-insoluble polymer.

The extended-release coating comprising a water-insoluble polymer further comprises a pore-former selected from the group comprising low viscosity grade hydroxypropyl methylcellulose having an apparent viscosity of less than 100 cP (2% in water at 20° C.), e.g., K3, E5, E15, and E50; sodium alginate; sugars and sugar alcohols, e.g., sucrose, dextrose, lactose, maltitol, and lactitol; low molecular weight polyethylene glycol (molecular weight of less than 3000); polyvinyl alcohol; polyvinyl pyrrolidone; hydroxypropyl cellulose; and mixtures thereof. Pore-formers may be present in an amount of 0% to 60% based on the weight of the extended-release layer.

According to another embodiment of this aspect, the extended-release layer comprises a mixture of ethyl cellulose and hydroxypropyl methylcellulose.

A second aspect of the present invention provides a process for preparation of an extended-release capsule dosage form of metoprolol succinate in the form of coated discrete units wherein the process comprises:
 a) coating inert cores with a solution or dispersion of metoprolol succinate to obtain drug layer coated cores;
 b) coating the drug layer coated cores of step a) with a solution or dispersion of an extended-release polymer; and
 c) filling the extended-release cores of step b) into suitable size capsules.

The dosage form may further comprise other pharmaceutically acceptable excipients.

Examples of pharmaceutically acceptable excipients include binders, diluents, lubricants/glidants, surfactants, and mixtures thereof.

Examples of binders include methyl cellulose, hydroxypropyl cellulose (HPC-L), carboxymethyl cellulose sodium, hydroxypropyl methylcellulose, polyvinylpyrrolidone, and mixtures thereof.

Examples of diluents include lactose, calcium carbonate, calcium phosphate, calcium sulfate, microcrystalline cellulose, cellulose powdered, fructose, lactitol, mannitol, sorbitol, starch, sucrose, and mixtures thereof.

Examples of lubricants or glidants include colloidal silicon dioxide, stearic acid, magnesium stearate, calcium stearate, talc, hydrogenated castor oil, sucrose esters of fatty acid, microcrystalline wax, yellow beeswax, white beeswax, and mixtures thereof.

Examples of surfactants include sodium lauryl sulfate, sodium dodecyl sulfate, ammonium lauryl sulfate, benzalkonium chloride, alkyl poly(ethylene oxide), copolymers of poly(ethylene oxide) and poly(propylene oxide) commercially known as poloxamers or poloxamines, polyvinyl alcohol (PVA), fatty alcohols, polyoxyethylene alkyl ether, polyoxyethylene alkylaryl ether, polyethylene glycol fatty acid ester, alkylene glycol fatty acid mono ester, sucrose fatty acid ester, sorbitol monolaurate (e.g., Span® or Span® 80), polyoxyethylene sorbitan fatty acid ester (polysorbates), and mixtures thereof.

The coating of the present invention may further comprise excipients selected from the group comprising plasticizers, binders, opacifiers, anti-tacking agents, anti-foaming agents, colors, film-forming polymers, and mixtures thereof. Organic or aqueous solvents may be used during the coating process. Solvents may be selected from the group comprising water, acetone, isopropyl alcohol, ethanol, isopropyl acetate, methylene chloride, and mixtures thereof.

Examples of plasticizers include propylene glycol, triethyl citrate, tributyl citrate, dibutyl sebacate, acetyl tributyl citrate, glyceryl monostearate, triacetin, polyethylene glycol, diethyl phthalate, acetylated monoglycerides, diacetylated monoglyceride, cetyl alcohol, and mixtures thereof.

Examples of opacifiers include titanium dioxide, silicon dioxide, talc, calcium carbonate, behenic acid, and mixtures thereof.

Examples of anti-tacking agents include talc, colloidal silicon dioxide, and mixtures thereof.

Examples of anti-foaming agents include silicon based surfactants, e.g., simethicone; vegetable oils; waxes; hydrophobic silica; polyethylene glycol; and mixtures thereof.

Coloring agents may be selected from FDA approved colorants such as iron oxide, lake of tartrazine, allura red, titanium dioxide, and mixtures thereof.

Examples of film-forming polymers include hydroxypropyl methylcellulose, methyl cellulose, carboxymethyl cellulose, hydroxyethyl cellulose, polyethylene glycol, polyvinyl alcohol, and mixtures thereof. Alternatively, commercially available coating compositions comprising film-forming polymers marketed under various trade names, such as Opadry®, may also be used for coating.

Coating may be carried out by using any conventional coating techniques known in the art, such as spray coating in a conventional coating pan, fluidized bed processor, or dry powder coating.

The following example illustrates the invention but is not to be construed as limiting the scope of the invention.

Example 1

| Ingredients | Quantity/Capsule (mg) |
| --- | --- |
| Drug Layer | |
| Metoprolol succinate USP equivalent to 25 mg of Metoprolol Tartrate, USP | 23.750 |
| Opadry ® clear | 2.375 |
| Sugar spheres | 18.750 |
| Purified water | q.s. |

-continued

| Ingredients | Quantity/Capsule (mg) |
|---|---|
| Extended-Release Layer | |
| Ethyl cellulose | 3.269 |
| Hydroxypropyl methylcellulose | 0.577 |
| Triethyl citrate | 0.096 |
| Isopropyl alcohol | q.s. |
| Talc | 0.096 |
| Purified water | q.s. |
| Lubrication | q.s. |
| Talc | 0.489 |

Manufacturing Process:

1) Metoprolol succinate and Opadry® clear were added to purified water to form a dispersion.

2) The dispersion of step 1) was sprayed onto sugar spheres to form drug coated cores.

3) Ethyl cellulose was dispersed in isopropyl alcohol and purified water.

4) Hydroxypropyl methylcellulose, talc, and triethyl citrate were added into the dispersion of step 3).

5) The dispersion of step 4) was sprayed onto the drug coated cores of step 2) to form extended-release discrete units.

6) The extended-release discrete units of step 5) were lubricated with talc.

7) The lubricated extended-release discrete units of step 6) were filled into size 4 capsule shells.

Dissolution Studies:

Dissolution tests were carried out using capsules prepared in Example 1 and Toprol-XL® tablet.

Dissolution was carried out in a USP type II apparatus, paddle rotating at 50 rpm, at a temperature of 37° C.±0.5° C., in 500 mL of pH 7.5 phosphate buffer.

TABLE 1

Dissolution profile of Example 1 and Toprol-XL® tablet.

| Time (hrs) | % Drug released (metoprolol succinate) in 500 mL of phosphate buffer | |
|---|---|---|
| | Toprol-XL® | Example 1 |
| 1 | 11 | 3 |
| 2 | 19 | 16 |
| 4 | 31 | 30 |
| 8 | 53 | 57 |
| 12 | 71 | 76 |
| 16 | 84 | 87 |
| 20 | 91 | 92 |

The results of the dissolution tests are shown in Table 1. It is evident that Example 1 provides a release profile which is comparable to Toprol-XL® tablet.

Simulation Studies:

The pharmacokinetic profile ($C_{max}$ and AUC) of Example 1 was predicted using software Phoenix WinNonlin® 6.4 and Phoenix IVIVC Toolkit 2.2. The predicted pharmacokinetic values of Example 1 was compared with pharmacokinetic values of Toprol-XL® tablet under fed and fasted conditions. Table 2 shows the simulated bioequivalence data of Example 1.

TABLE 2

Simulated T/R ratio for Example 1 w.r.t Toprol-XL® tablet

| Parameter | Fed T/R Ratio | Fasted T/R Ratio |
|---|---|---|
| $AUC_{last}$ | 1.03 | 0.95 |
| $C_{max}$ | 1.03 | 1.09 |

From the above data it is evident that metoprolol extended release capsules of Example 1 would be bioequivalent to Toprol-XL® tablet under fed and fasted conditions.

We claim:

1. An extended-release capsule dosage form of metoprolol succinate in the form of coated discrete units, wherein the capsule dosage form comprises metoprolol succinate in an amount of about 30% to about 70% by the total weight of the dosage form and is bioequivalent to the marketed extended release tablet of metoprolol succinate.

2. The extended-release capsule dosage form according to claim 1, wherein the capsule is in the form of a sprinkle capsule.

3. The extended-release capsule dosage form according to claim 1, wherein the coated discrete units have a particle size from about 0.2 mm to 2.5 mm.

4. The extended-release capsule dosage form according to claim 1, wherein the coated discrete units are coated inert core in the form of plurality of pellets, granules, minitablets, or beads.

5. The extended-release capsule dosage form according to claim 1, wherein the coated discrete units comprise
   a) inert cores;
   b) a drug layer over the inert cores comprising metoprolol succinate; and
   c) an extended release layer over the drug layer coated cores.

6. The extended-release capsule dosage form according to claim 5, wherein the inert cores are water-soluble or water-swellable.

7. The extended-release capsule dosage form according to claim 6, wherein the water-soluble or water-swellable inert cores are made up of sugar, microcrystalline cellulose, cellulose, starch, modified starch, or mixtures thereof.

8. The extended-release capsule dosage form according to claim 7, wherein the sugar is selected from the group consisting of glucose, mannitol, lactose, xylitol, dextrose, and sucrose.

9. The extended-release capsule dosage form according to claim 5, wherein the extended-release layer comprises an extended-release polymer in an amount of about 5% to about 20% based on the weight of drug layer coated cores.

10. The extended-release capsule dosage form according to claim 9, wherein the extended-release polymer is selected from the group consisting of water-soluble/swellable polymers, water-insoluble polymers, and mixtures thereof.

11. The extended-release capsule dosage form according to claim 10, wherein the water-soluble polymer is selected from the group consisting of hydroxypropyl methyl cellulose, hydroxyethyl cellulose, polyethylene glycol, poly(ethylene oxide), hydroxypropyl cellulose, carboxymethyl cellulose, xanthan gum, starch, and mixtures thereof.

12. The extended-release capsule dosage form according to claim 10, wherein the water-insoluble polymer is selected from the group consisting of cellulose ethers, cellulose esters, polymethacrylic acid esters copolymers, aminoalkyl methacrylate copolymers, copolymers of polyvinyl acetate and polyvinyl pyrrolidone, and mixtures thereof.

13. The extended-release capsule dosage form according to claim 12, wherein the cellulose ether is ethyl cellulose.

14. The extended-release capsule dosage form according to claim 12, wherein the water-insoluble polymer further comprises a pore-former.

15. The extended-release capsule dosage form according to claim 14, wherein the pore-former is selected from the group consisting of low viscosity grade hydroxypropyl methylcellulose, sodium alginate, sugars and sugar alcohols, low molecular weight polyethylene glycol, polyvinyl alcohol, and mixtures thereof.

16. An extended-release sprinkle capsule dosage form of metoprolol succinate comprising coated discrete units, having a particle size from about 0.2 mm to 2.5 mm, wherein the capsule dosage form releases not less than 15% of metoprolol succinate after 4 hours, when measured in a United States Pharmacopeia (USP) type 2 dissolution apparatus, paddle at 50 rpm, at a temperature of 37° C.±0.5° C. in 500 mL of pH 7.5 phosphate buffer.

17. The extended-release sprinkle capsule dosage form according to claim 16, wherein the capsule dosage form releases about 15% to about 45% of metoprolol succinate after 4 hours, when measured in a United States Pharmacopeia (USP) type 2 dissolution apparatus, paddle at 50 rpm, at a temperature of 37° C.±0.5° C. in 500 mL of pH 7.5 phosphate buffer.

18. An extended-release sprinkle capsule dosage form of metoprolol succinate comprising coated discrete units, having a particle size from about 0.2 mm to 2.5 mm, wherein the capsule dosage form exhibits the following in-vitro dissolution profile, when measured in a United States Pharmacopeia (USP) type 2 dissolution apparatus, paddle at 50 rpm, at a temperature of 37° C.±0.5° C. in 500 mL of pH 7.5 phosphate buffer: a) not less than 15% of metoprolol succinate is released after 4 hours; and b) not less than 60% of metoprolol succinate is released after 12 hours.

19. The extended-release sprinkle capsule dosage form according to claim 16 wherein the capsule dosage form comprises metoprolol succinate in an amount of about 30% to about 70% by the total weight of the dosage form.

* * * * *